United States Patent [19]

Moore

[11] Plant 4,447

[45] Aug. 7, 1979

[54] MINIATURE ROSE PLANT

[76] Inventor: Ralph S. Moore, 2519 E. Noble Ave., Visalia, Calif. 93277

[21] Appl. No.: 935,617

[22] Filed: Aug. 21, 1978

[51] Int. Cl.[2] ..... A01H 5/00

[52] U.S. Cl. ..... Plt./8

[58] Field of Search ..... Plt./8

*Primary Examiner*—Robert E. Bagwill

[57] ABSTRACT

The subject of the present disclosure is a new and distinct variety of miniature rose plant characterized by the yellow color of buds and flowers and further identified by the unique "moss" on the buds, said moss being soft to the touch and fragrant (lemon).

6 Drawing Figures

1

The present invention relates to a new and distinct variety of hardy, dwarf, bush type rose plant of the miniature class; the variety being primarily characterized — as to novelty — by medium yellow buds and flowers which in general color effect are similar to Yellow Jewel, miniature (U.S. Plant Pat. No. 3,827).

The variety is further characterized by:

Mossed buds, said moss being soft to the touch, and which gives off a lemony fragrance when the mossy bud is touched or rubbed.

An abundance of bloom, with flowers borne singly or several to the stem in loose clusters.

Light sweet fragrance.

A plant which is vigorous, of rounded somewhat spreading shape with semi-glossy (to matt) small foliage with pointed leaflets; the buds and flowers being similar in form and size to Yellow Jewel (miniature — U.S. Plant Pat. No. 3,827).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Fairy Moss (U.S. Plant Pat. No. 3,082) as the seed parent and Goldmoss — Floribunda moss rose, (U.S. Plant Pat. No. 3,563), as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—LEMON DELIGHT.

2

Flowers borne: Singly and several together (3 to 5) on slender, wirey, quite thorny, stems.

Quantity of bloom: Abundant both outside and in greenhouse.

Bud:

*Peduncle.*—Medium length; slender but sturdy; erect; medium to light green. Hairs — numerous hairs and thorns.

*Before calyx breaks.*—Size — small. Form long: pointed with numerous soft hairs and moss-like appendages on surface of bud; with foliaceous parts extending beyond the tip of the bud equal to one-half or less of its length. Color — medium green.

*As calyx breaks.*—Color — medium yellow — near Buttercup Yellow 5/2.

*Opening.*—Opens well in all weather.

Bloom:

*Size when fully open.*—Small, averaging about 40 mm (1½").

*Petalage.*—Semi-double — averaging about 12 petals, arranged regularly plus sometimes one or more occasional petaloids.

*Form.*—Cupped at first, becoming more open, with petals rolled loosely outward, and later at maturity open with petals remaining in similar shape and position. Open flowers show stamens.

Petals: Fairly thick; satiny on inside and on outside surface. Shape — outside petals, broad lanceolate (nearly oval) with acute tip; intermediate — broad lanceolate with acute tip; inside — lanceolate with acute or rounded tip.

Color: Newly opened flower from a plant grown outdoors:

*Outside petal.*—Outside surface — near Buttercup Yellow 5/2 becoming slightly greenish toward base. Inside surface — near Buttercup Yellow 5/2 becoming a deeper yellow at base.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — color medium yellow. Three days open — color similar to newly opened flowers but lighter color. Behavior — opens well in all weather. Spent petals drop off. Flower longevity (May 1978) — plant in pot 4–5 days. Cut flowers at living room temperature 3–4 days.

Reproductive Organs:

*Stamens.*—Abundant, arranged regularly about pistils.

*Filaments.*—Varying length, medium to long, yellow.

*Anthers.*—Well formed; yellow.

*Pollen.*—Abundant amount.

*Pistils.*—Average number.

*Styles.*—Fairly even; medium length; bunched; color — greenish.

*Ovaries.*—All enclosed in calyx.

*Hips.*—Numerous. Hips are covered with numerous slender thorns and prickles of varying length.

*Sepals.*—Permanent; spear shaped; recurved.

*Seed.*—Several.

Foliage:

*Leaves.*—Compound of five or seven leaflets — if growth is vigorous, seven is the usual number; quite small; leathery; semi-glossy to matt.

*Leaflets.*—Shape: broad lanceolate; nearly oval; apex acute; base rounded or rounded acute. Margin serrate.

*Color.*—Medium green; new growth — normal (medium) green.

*Rachis.*—Medium strength; upper side may have numerous tiny short hairs or prickles, grooved; underside moderately thorny with several short hairs and tiny prickles.

*Stipules.*—Medium long; narrow to medium width; short length narrow points which turn out usually at more than 45 degrees.

Growth:

*Habit.*—Dwarf; bushy; rounded; much branched.

*Growth.*—Free vigorous; internodes short.

*Canes.*—Medium, slender; sturdy.

*Main stems.*—Color: medium green.

*Thorns.*—Many; slender; hooked slightly downward; color; gray. Prickles — numerous; hairs — none. Branches — color: light to medium green. Thorns: numerous; medium length; slender; nearly straight, inclined slightly downward. Medium to short oval base. Prickles: numerous. Hairs: some. Young shoots — color: light to medium green. Thorns numerous, slender; nearly straight, inclined slightly downward; color — greenish.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described characterized by buds and flowers which are (1) clear medium yellow in color, the buds and flowers resembling Yellow Jewel (miniature — U.S. Plant Pat. No. 3,827) in size and shape and (2) the bud (sepals) being well covered with short moss, said moss being soft to the touch and giving off a lemon-like fragrance when rubbed or brushed; and further characterized by a plant which is vigorous and compact, easy to propagate from soft wood cuttings or by budding, with an abundance of flowers borne singly or several to the stem in loose clusters.

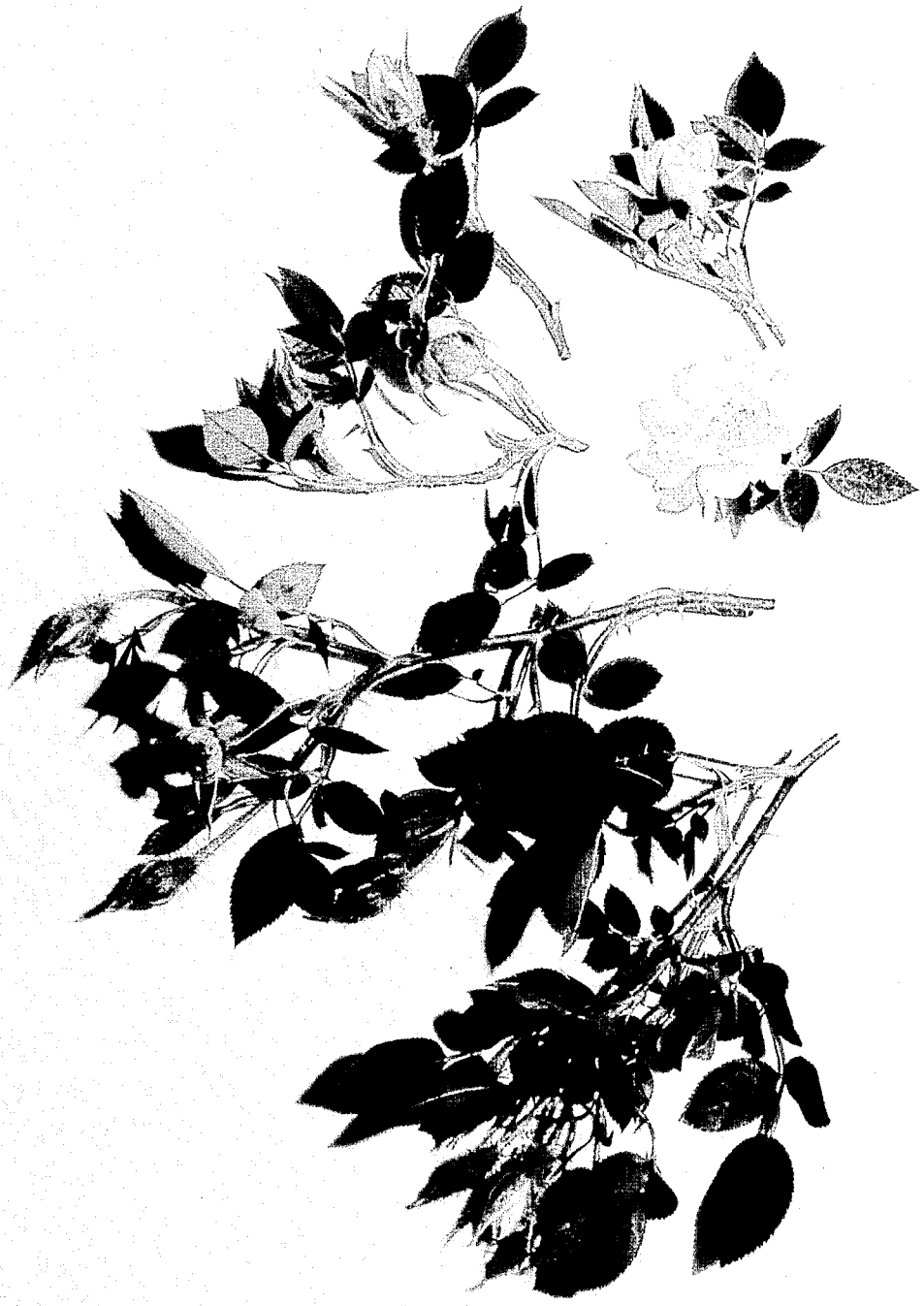

* * * * *